(12) United States Patent
Raupach et al.

(10) Patent No.: US 8,778,167 B2
(45) Date of Patent: Jul. 15, 2014

(54) METHOD AND DEVICE FOR DETERMINING THE LOCATION OF CORROSION SITES IN REINFORCED CONCRETE

(75) Inventors: Michael Raupach, Aachen (DE); Kenji Reichling, Aachen (DE)

(73) Assignee: Rheinisch-Westfaelische-Technische Hochschule Aachen, Aachen (DE)

( * ) Notice: Subject to any disclaimer, the term of this patent is extended or adjusted under 35 U.S.C. 154(b) by 0 days.

(21) Appl. No.: 13/266,136

(22) PCT Filed: May 31, 2010

(86) PCT No.: PCT/EP2010/003292
§ 371 (c)(1),
(2), (4) Date: Nov. 15, 2011

(87) PCT Pub. No.: WO2010/145753
PCT Pub. Date: Dec. 23, 2010

(65) Prior Publication Data
US 2012/0080325 A1 Apr. 5, 2012

(30) Foreign Application Priority Data
Jun. 19, 2009 (DE) .......................... 10 2009 029 914

(51) Int. Cl.
*G01N 17/02* (2006.01)
*G01N 17/04* (2006.01)

(52) U.S. Cl.
CPC ................ *G01N 17/02* (2013.01); *G01N 17/04* (2013.01)
USPC ..................... 205/776.5; 205/775.5; 205/724; 204/404

(58) Field of Classification Search
CPC ................................ G01N 17/02; G01N 17/04
USPC .................... 204/404; 205/775.5, 776.5, 724; 324/71.1, 508, 700; 702/22, 30–32, 702/35–38, 58, 59
See application file for complete search history.

(56) References Cited

U.S. PATENT DOCUMENTS

| 4,584,530 A | 4/1986 | Nicholson |
| 4,758,324 A | 7/1988 | Winneti |
| 4,942,354 A | 7/1990 | Miller |
| 6,582,587 B1 * | 6/2003 | Srinivasan et al. ............ 205/724 |

FOREIGN PATENT DOCUMENTS

| CH | 683719 B | 4/1994 | |
| GB | 2157441 A | 10/1985 | |
| WO | 2007/096668 A1 * | 8/2007 | ............ G01N 17/02 |
| WO | 2007096668 A | 8/2007 | |

OTHER PUBLICATIONS

Elsener et al. (Materials and Structures vol. 36 pp. 461-471).*
Proceq (Operating Instructions, Corrosion Analyzing Instrument, published Jan. 2009).*
Marsh et al. (Journal of Structural Engineering, Jun. 2007, pp. 777-787).*
Borenstein (International Conference on Intelligent Robots and Systems (IROS '94)—Advanced Robotic Systems and the Real World., Munich, Germany, Sep. 12-16, 1994, pp. 127-134).*

* cited by examiner

*Primary Examiner* — Luan Van
*Assistant Examiner* — Steven Rosenwald
(74) *Attorney, Agent, or Firm* — Andrew Wilford (57) ABSTRACT

The invention relates to a method for determining the location of the corrosion sites in reinforced concrete, wherein a value (UB, UC) of a voltage potential (UB, UC) present at each measurement location is measured at at least two measurement locations relative to a reference voltage potential (UA) present at a reference location, and information about the direction to the corrosion site (K) and/or the distance to the corrosion site (K) is determined from the location information (XB, YB, XC, YC) for each measurement location, particularly also the reference location, and the voltage potential (UA, UB, UC) present at each location. The invention further relates to a device for determining the location of corrosion sites in reinforced concrete, particularly according to a method according to one of the previous claims, comprising an electrode arrangement having at least one electrode that can be brought into electrolytic contact with the surface of a reinforced concrete to be tested, and that is set up for measuring voltage potentials (UB, UC) using the at least one electrode at a plurality of measurement locations relative to a reference voltage potential (UA) at the reference location of an electrode, and that is further set up for determining information about the direction to the corrosion site (K) and/or the distance to the corrosion site (K) from the location information (XB, YB, XC, YC) for each measurement location, particularly also the reference location, and the voltage potential (UA, UB, UC) present at each location.

12 Claims, 5 Drawing Sheets

CALCULATION OF THE NORMAL VECTOR

Point direction form:

$$\bar{x} = \begin{pmatrix} XA \\ YA \\ UA \end{pmatrix} + t \cdot \begin{pmatrix} XB - XA \\ YB - YA \\ UB - UA \end{pmatrix} + S \cdot \begin{pmatrix} XC - XA \\ YC - YA \\ UC - UA \end{pmatrix}$$

Calculation of the normal vector:

$$\underline{t} : (XB - XA) \cdot nx + (YB - YA) \cdot ny + (UB - UA) \cdot nz = 0$$

$$\Rightarrow nx = -\frac{(YB - YA) \cdot ny}{XB - XA} - \frac{(UB - UA)}{XB - XA} \cdot nz$$

$$\underline{s} : (XC - XA) \cdot nx + (YC - YA) \cdot ny + (UC - UA) \cdot nz = 0$$

with $n_x$ from $t$ in $s$:

$$-(XC - XA) \cdot \left[ \frac{YB - YA}{XB - XA} \cdot ny + \frac{UB - UA}{XB - XA} \cdot nz \right]$$
$$+ (YC - YA) \cdot ny + (UC - UA) \cdot nz = 0$$

$$\Leftrightarrow nz \cdot \left[ -\frac{(XC - XA) \cdot (UB - UA)}{(XB - XA)} + (UC - UA) \right]$$

$$+ ny \cdot \left[ -\frac{(YB - YA) \cdot (XC - XA)}{(XB - XA)} + (YC - YA) \right] = 0$$

$$\Leftrightarrow nz = \underbrace{\frac{\left[ \frac{(YB - YA) \cdot (XC - XA)}{(X_B - X_A)} - (YC - YA) \right]}{\left[ -\frac{(XC - XA) \cdot (UB - UA)}{(XB - XA)} + (UC - UA) \right]}}_{G} \cdot ny$$

with $n_z = G \cdot n_y$ in $t$:

$$nx = -\frac{[(YB - YA) + (UB - UA) \cdot G]}{(XB - XA)} \cdot ny$$

Since the equation system is not solvable $n_y = 1$ is assumed and one gets:

$$\bar{n}(ny) = \begin{pmatrix} nx \\ ny \\ nz \end{pmatrix} \Rightarrow \bar{n} = \begin{pmatrix} nx \\ 1 \\ nz \end{pmatrix} \text{ und } |\bar{n}| = \sqrt{nx^2 + ny^2 + nz^2}$$

Fig. 4A

The averaged normal vector is calculated as follows:

$$\vec{n}1 = \begin{pmatrix} \dfrac{nx}{|\vec{n}|} \\ \dfrac{ny}{|\vec{n}|} \\ \dfrac{nz}{|\vec{n}|} \end{pmatrix} = \begin{pmatrix} n1,x \\ n1,y \\ n1,z \end{pmatrix}$$

The projection length in the x-y plane:

$$L = \sqrt{n1,x^2 + n1,y^2}$$

The angle to the y axis is calculated as:

$$\alpha = \arctan\left(\dfrac{n1,x}{n1,y}\right)$$

*Fig. 4B*

METHOD AND DEVICE FOR DETERMINING THE LOCATION OF CORROSION SITES IN REINFORCED CONCRETE

CROSS REFERENCE TO RELATED APPLICATIONS

This application is the US-national stage of PCT application PCT/EP2010/003292 filed 31 May 2010, published 23 Dec. 2010 as WO 2010/145753, and claiming the priority of German patent application 102009029914.9 itself filed 19 Jun. 2009.

FIELD OF THE INVENTION

The invention relates to a method of determining the location of corrosion sites in reinforced concrete, for example ferroconcrete or prestressed concrete. The invention furthermore relates also to an apparatus for determining the location of corrosion sites in reinforced concrete, particularly one with which the method according to the invention can be carried out.

BACKGROUND OF THE INVENTION

Concrete is usually provided with reinforcement in order to increase its load-bearing capacity. This reinforcement typically involves concrete rod steels or mat reinforcement (reinforcement rods provided in a grid pattern), around which the concrete mass is poured during construction.

In this connection, it is known that a thin oxide layer forms on the metal reinforcements in the highly alkaline environment produced by the concrete, the layer protecting against further corrosion. However, it is known as a problem that the protective oxide layer can be destroyed by external influences, for example as the result of chlorides that penetrate the concrete all the way to the reinforcement, or also as the result of carbonization of the concrete, thereby making it possible for defects in the passive oxide layer to form, and therefore defects that form locally can corrode further, particularly under the influence of oxygen and moisture that are normally present in the concrete.

Accordingly, a ferroconcrete structure can lose its load-bearing capacity as the result of advancing corrosion of the reinforcements, and can become a safety risk. It is therefore known in the state of the art to find such corrosion sites by measurement technology measures, for example by the principle of half-cell potential measurement.

This principle takes advantage of the fact that a corrosion site, which can be referred to as base, forms an electrogalvanic cell together with the precious, corrosion-protecting regions of a reinforcement rod, which means that the formation of a potential funnel occurs in the surroundings of the corrosion site, and also that minimal current flows arise.

The method known in the prior art makes use of this, namely in that an electrode referred to as a half cell is contacted with the surface of the concrete, with another contact with a metal reinforcement (armoring) to be investigated being produced by way of a voltmeter, to which end it is necessary to break the concrete up locally in order to obtain access to the reinforcement to be investigated. There is then the possibility of measuring the potentials that have occurred at the local corrosion site that extend all the way to the surface of the concrete, relative to a reference potential, with direct contacting of the metal reinforcement, and of drawing conclusions concerning the position of a corrosion site from the value of the measured potential.

In this connection, it is felt to be disadvantageous, on the one hand, that a measured potential in and of itself does not make sufficient information available so that a conclusion can be drawn concerning the location of a corrosion site, and, on the other hand, it is considered to be particularly disadvantageous that access through the concrete all the way to a metal reinforcement must be created mechanically, by destructive measures, in order to obtain a reference potential. Creation of such access is cost-intensive, time-consuming, and furthermore requires renewed closing of the access point that has been created, after the measurement has been made. Another disadvantage is considered to be the cable connection with the reinforcement connector, where usually very great cable lengths are required.

OBJECT OF THE INVENTION

It is therefore the object of the invention to provide a method and an apparatus by means of which more precise information about the location of the corrosion site can be obtained from measurements of potentials, and with which corrosion sites on the reinforcement rods of reinforced concrete can be found, preferably in a destruction-free manner and with great precision. In this connection, in a preferred embodiment, the possibility is supposed to be created, using the apparatus and the method, of not only undertaking measurements of concrete surfaces on a point by point basis, but also of scanning a given concrete surface and obtaining information concerning corrosion sites in the interior of the concrete from the data of such a scan, and of directly representing the sites graphically.

SUMMARY OF THE INVENTION

According to the invention, this object is attained in that a value of the voltage potential existing at the measurement location in question is measured on the concrete surface, at least at two measurement locations, relative to a reference voltage potential existing at a reference location, where information about the direction toward the corrosion site and/or the distance to the corrosion site can be determined from location information concerning each measurement location and, if necessary, also concerning the reference location and the voltage potential existing at each measurement location, and/or this can also involve qualitative information. With regard to the distance, this distance can therefore be calculated in concrete terms, in a dimensional unit, in one embodiment, for example, or the information can be provided by the mere statement "far" or "close," if necessary with several gradations.

Such a determination can take place mathematically, for example, by calculation using a data-processing system, particularly taking into consideration physical knowledge of potentials in the surroundings of corrosion sites, and, in particular, of their spatial arrangement or configuration. Thus, the information can be obtained solely from the data about the amount of the voltage potentials and the location at which a voltage potential (if applicable, including a respective reference voltage potential) prevails, taking into consideration physical fundamentals or a physical model.

In an illustrated embodiment, a 3D spatial coordinate can be formed from the 2D coordinates of the measurement locations, particularly also of the reference location, in a plane of a predetermined coordinate system, particularly one that is selected parallel to or on the surface of the concrete, together with the value of the potential at the location in question; each of these coordinates determines a point in the coordinate system. Then, information about the direction toward the corrosion site and/or the distance to the corrosion site can be determined mathematically from at least three points. In this connection, one of the three points can be given by the coordinates of the reference location and its reference voltage potential, but it can also be provided that all the points are formed by measurement locations and voltage potentials that are measured in concrete terms.

It is essential for the method according to the invention that voltage potentials are recorded at a plurality of measurement locations. With the knowledge that voltage potentials are location-dependent relative to the corrosion site, the desired information can accordingly be calculated, for example in that points in the space of the selected coordinate system are determined using the measurements and the 2D location coordinates at least of the measurement sites and, if applicable, also of the reference site, and of the potential of the latter, which is assumed to be zero or standardized.

These points lie on the surface of a potential funnel existing around the corrosion site, and thereby represent information about the position and size/height of the potential funnel in space, i.e. the selected coordinate system. Information is about the potential funnel and thus the location of a corrosion site can therefore be determined, by mathematical calculations, from the three points.

Measurement of the voltage potentials at different measurement locations relative to a reference location can take place, in one embodiment for example, by a single electrode that is electrolytically contacted with the surface of the concrete. The voltage potential can be measured at a plurality of measurement locations, one after the other, by this electrode, relative to an electrode at a reference location. In this connection, the reference location can be on the concrete surface, or it can also be represented by a reinforcement in the interior of the concrete that was partially broken up to create access to the reinforcement. Preferably, the reference location should be maintained for every measurement at every measurement location.

In another embodiment, a plurality of electrodes can also be used for measuring the voltage potentials relative to an electrode at a reference location, which electrodes are electrolytically contacted with the surface of the concrete. Thus, the possibility exists of undertaking the potential measurement at least at two measurement locations, by at least two electrodes of which one is assigned to each measurement location at the time of the measurement. In this connection, the reference location can be on the concrete surface, or it can also be represented by a reinforcement in the interior of the concrete that was partially broken up in order to create access to the reinforcement.

Here, the two electrodes that define the measurement locations can preferably be provided in a fixed location, in an electrode array, defined relative to one another. The electrode at the reference location can be separate from this, or can also form part of the electrode array. In the latter case, the electrode at the reference location is also fixed in place relative to the electrodes at the measurement locations, and in this connection preferably also electrolytically contacts the concrete surface.

Whenever an electrode is contacted with the concrete surface at the reference location, this preferably takes place electrolytically. For example, a reference electrode can also be attached to a reinforcement in clamping manner, by direct metal contact.

In the method according to the invention, the possibility also exists of first carrying out a plurality of potential measurements at different measurement locations, preferably always relative to the same reference location, and of forming the 3D coordinate and the corresponding point in space for each measurement location, if applicable also the reference location, and then subsequently calculating information about the direction toward and/or the distance from a corrosion site from the collective of all the points in space formed in this manner by each of at least three points.

Alternatively, the voltage potentials relative to a reference location can also be measured, one after the other, using groups of at least two measurement locations, and the three points can be formed in a related measurement step, and then the information concerning direction and/or distance can be calculated for each, before the method is continued with the measurement of the voltage potentials at a next group of at least two measurement locations. In this connection, the reference location can change from point to point, or can also be maintained for all the groups.

First of all, a coordinate system must be defined or predetermined, in order to carry out the method according to the invention, at least if a review of the concrete surface is to be carried out at a plurality of locations, particularly an area-wide review of a concrete surface is to be carried out at more than one location, and the measurements at the many different measurement positions are supposed to be put into correlation with one another.

For this purpose, an origin can be defined, in any desired manner, which origin lies on the concrete surface, for example. A 2D coordinate of each measurement location or of the electrode at each measurement location can accordingly be determined relative to this formed or selected origin, for example also by measurement technology determination.

For example, it can be determined, in this manner, that the electrode has the 2D coordinate (X1, Y1) at a measurement location 1, the (same or different) electrode has the 2D coordinate (X2, Y2) at a measurement location 2, and the electrode has the coordinate (X3, Y3) at the reference location 3, when the method or the apparatus is restricted to three points to be determined, in this consideration of an example, where it should be pointed out that the method or the apparatus for implementing the method can also work with more than two measurement locations and one reference location. In particular, the method can be carried out with any desired number of N measurement locations and a reference location.

In the measurement using an electrode array having electrodes fixed in place, particularly at the measurement locations and the reference location, the configuration of the electrodes in general, for example, can be selected in such a manner that the electrodes, i.e. their contact locations on the concrete surface, describe a geometrical, particularly a symmetrical shape, in other words, for example, three electrodes are provided in a triangular shape, in which the electrodes are provided in the corners of the triangle, particularly an equilateral triangle. Four electrodes can describe a quadrangular shape, particularly a square shape, or, alternatively, also a triangular shape, in which three of the four electrodes are provided in the corners of the triangle and one of the four electrodes is provided in the geometrical center of gravity of the triangle. Such an arrangement with electrodes fixed in place has the advantage that if at least the 2D coordinates of one of these electrodes, particularly an electrode at a measurement location, are known, the 2D coordinates of the other locations (measurement and/or reference location) or electrodes can be directly calculated from this, because all the electrodes, relative to one another, have a known, locally fixed arrangement.

The potential at each of the electrodes being considered can be represented by a value, specifically, for two electrodes, by a respective measurement relative to the electrode at the reference location, where here, it can be provided that the reference potential at this electrode is defined as zero.

In the case of such an electrode array, it is preferably provided that this array has at least three electrodes fixed in place relative to one another, where it can be provided, according to the method, to bring all the electrodes of this electrode array into electrolytic contact with the surface of a reinforced concrete to be tested. In order to obtain an array in a fixed location, the electrodes can be attached to a common frame or electrode carrier, for example.

The method according to the invention, in this preferred further development, decisively distinguishes itself from the previously known state of the art, namely in that there is no need to obtain direct access to a reinforcement in the interior of the concrete volume by destruction of the concrete. Instead, the method according to the invention, in this embodiment, finds it is entirely sufficient to bring the electrodes of the electrode array into contact with the reinforced concrete to be tested merely at the surface.

It is furthermore provided to then measure voltage potentials between the electrodes, where preferably, one of the electrodes of the electrode array is at the reference location, in order to measure the voltage potentials at the locations of the other electrodes of the electrode array relative to this electrode.

Thus, the respective potentials can be measured at the other, at least two further electrodes of the electrode array, at the measurement locations, i.e. it can particularly be recorded and preferably also stored in memory, at least for the duration of the subsequent further processing, relative to the electrode at the reference location, particularly at the location where the potential can be defined as zero by computation technology, for example.

Independent of whether the potential measurements are carried out using an array of a plurality of electrodes, particularly electrodes fixed in place relative to one another, or one after the other, using only one electrode at a plurality of measurement locations, 3D spatial coordinates can accordingly be formed, together with the 2D coordinates of an electrode, at every reference location, if necessary also at the reference location, namely in that it is assumed that the 2D coordinates are situated in a plane of the selected coordinate system, particularly in a plane of the concrete surface or parallel to it. This plane can be defined as an x-y plane, where the value of a potential can then form a z coordinate. The coordinate designations can be interchanged as desired, without changing the essential idea of the invention.

Accordingly, using the method according to the invention, a number of at least three 3D spatial coordinates (at at least two measurement locations and one reference location) are obtained that have the coordinate (X1, Y1, U1), the further coordinate (X2, Y2, U2), as well as the third 3D spatial coordinate (X3, Y3, U3), with reference to the above-described example. In this connection, the values U1 and U2 represent the measurements of the voltage potential at the measurement locations 1 and 2 relative to the reference location, at which the potential is assumed to be zero or defined as zero. The position of a point in the space of the selected coordinate system is described by each of the three 3D spatial coordinates. In this connection, it is unimportant whether this is a coordinate system with Cartesian or polar coordinates, or coordinates of a different definition.

In the case of a correspondingly higher number of electrodes, the above-described deliberation applies analogously, with a correspondingly higher number of points in the selected coordinate system.

Now, according to the invention, the distance to and/or the direction toward the corrosion site can be determined using the three points formed by the invention, which points lie on a potential funnel of a corrosion site.

This can take place by fundamentally any desired method of procedure by means of which conclusions are drawn concerning the shape and/or location and/or height of the potential funnel, based on the geometric location of the points in space. For example, this can be done by purely trigonometric or also vectorial calculations.

In a preferred method variant, for a plane defined by the three points, a measure for the gradient of this plane or a variable that depends on it can be determined, where the direction toward a corrosion site and/or a distance to a corrosion site is then calculated from this measure or the variable. In this connection, the gradient is all the greater, in terms of amount, the less the distance to the corrosion site. In this connection, the vectorial direction of the gradient points to the corrosion site.

In an example, the distance and/or the direction can be determined from the mathematical projection of the standardized normal vector of the plane (by the three points) in a plane of the coordinate system that lies in or parallel to the concrete surface, where the direction is represented by the expanse of the projected normal vector, and the distance is represented by its length.

For example, this is the projection into the x-y plane of the coordinate system or a plane parallel to it. In this connection, the direction is understood to be an angle relative to one of the coordinate axes x or y of the coordinate system. In this connection, the location in the coordinate system for which the distance to the corrosion site is determined is essentially the location at which the normal vector is positioned on the plane, in terms of calculations.

To carry out the above-described method step, it can be provided that a mathematical plane that comprises the points determined by the spatial coordinates is generated by calculations. For this purpose, a mathematical representation of the plane can be calculated by a data-processing system, for example, on the basis of the three points or their 3D spatial coordinates.

The method step of the formation of such a mathematical plane is based on the deliberation that a potential funnel forms around a corrosion site (considered in ideal terms) in this way, as was explained initially. Three points on such a potential funnel are determined by measuring or determining the potential at least at three locations in the surroundings of such a corrosion site, where here, however, for simplification, only the ideal potential funnel shape is assumed, but in practice, due to deviations from ideal conditions, potentials that are not funnel-shaped will form. In this connection, in a further development, potentials that do not have the ideal funnel shape can also be taken into consideration in the calculation.

A plane that is formed by at least three measurement locations accordingly intersects the potential surface or potential funnel in the surroundings of a corrosion site, and would lie tangentially against the potential surface if one were to lay the locations of the three electrodes infinitesimally against one another, in idealized manner. Within the scope of the measurement precision existing as the result of the actual spatial spacing of the measurement locations or of the electrodes used for the measurement, accordingly such a plane between the three determined points approximately represents a surface segment of the potential surface.

Once the mathematical plane has been determined in such a manner, it can furthermore be provided, according to the invention, to determine the standardized normal vector relative to this plane by calculations, which vector stands on this plane with the standardized length 1, has its origin in it, and points in a direction away from the plane, particularly in a direction toward the interior of the potential funnel. It can then furthermore be provided to project the standardized normal vector that has been determined by calculations mathematically into the x-y plane of the coordinate system, particularly into the plane of the concrete surface or a plane parallel to it, and to determine the length and the direction of the normal vector projected in this manner.

This results in two values determined using the method, which contribute to localization of a corrosion site, namely in such a manner that the direction that the normal vector has in the projection points in the direction of a corrosion site, and the length of the projection is a measure of the distance of the electrode array from the corrosion site. The length of the projected standardized normal vector is a measure of the amount of the gradient of the plane.

This, in turn, is based on the deliberation, in idealized manner, that in the case of a potential funnel that is assumed to be ideal, every normal vector that stands on the inner funnel surface points precisely into the center of the funnel and thus toward the corrosion site in the projection onto a plane parallel to the concrete surface or the x-y plane. In this connection, the projection has the greatest length, namely the length 1 for the standardized normal vector at the location of the funnel where the assumed ideal funnel wall stands perpendicular to the x-y plane. In the direction toward the outside, on the other hand, the steepness of the funnel wall decreases, i.e. the projection of the normal vector is less than 1 and becomes less with an increasing distance.

The method described here can be carried out using an apparatus that comprises an electrode array having at least one electrode at a measurement location that can be brought into electrolytic contact with the surface of a reinforced concrete to be tested, where the apparatus is set up to measure voltage potentials at a plurality of measurement locations, relative to a reference potential at a reference location, using the one electrode, and which is furthermore set up to form a 3D spatial coordinate relative to the origin of a predetermined coordinate system, for every measurement location, from its 2D coordinate in a plane in or parallel to the concrete surface, together with a value that represents the respective potential at this measurement location, which 3D coordinate defines a point in the space of the respective coordinate system, particularly by running a software in a data-processing part of the apparatus, and to determine the distance and/or the direction to a corrosion site from at least three points determined in this manner.

Then, the voltage potential relative to an electrode at the reference location can also be measured at a plurality of measurement locations, using a single electrode in the electrode array.

In order to simplify the measurement, however, it can be provided, in a preferred further development, that the electrode array comprises at least two electrodes provided in a fixed position relative to one another that can be brought into electrolytic contact with the surface of a concrete to be tested. An electrode at the reference location can be separate from this array.

However, in a further preferred electrode array, it can form part of this electrode array. Then, an electrode array according to the invention has at least three electrodes, at least two of which form the electrodes at the measurement location and one forms the electrode at the reference location.

The determination of distance and direction to the corrosion site can take place, in this connection, by the apparatus or a data-processing system provided in it, as was described above.

In this connection, it should be stated that in the sense of the invention for method and apparatus, in the case of the one stated embodiment using a projection of a standardized normal vector, it is not necessary, after the three points have been obtained, to first calculate a mathematical representation of the plane through these points by individual calculation steps, proceeding from calculating the normal vector in a mathematical representation, undertaking the projection by further mathematical representation, and then determining the direction and/or the length using the latter.

Instead, it can also be provided to directly calculate those values that correspond to the length and/or the direction of the projected standardized normal vector, by a single mathematical step or by application of a calculation algorithm to the three points. However, the implementation of such a calculation step, for example by a formulaic relationship, corresponds, in terms of content, to the implementation of the above-described steps, without an intermediate representation by mathematical values having to be given for each of these steps.

This consideration furthermore applies also for subsequent method steps of a mathematical nature that do not necessarily have to be carried out discretely, but are taken into consideration in the calculation of the direction and length of the normal vector in a formulaic relationship. Furthermore, the apparatus can also be used to determine information about the direction to the corrosion site and/or the distance from it, using other mathematical calculations.

In a further development of the method that makes use of the projection of the normal vector, it can be provided that the normal vector is laid into a sector of the determined plane that is delimited by a polygon, the corner points of which are given by the three points or their 3D spatial coordinates, for the purpose of the projection.

This method step is based on the deliberation that a normal vector can fundamentally be positioned at any desired location perpendicular to a mathematical plane that extends infinitely in space. For the present method, positioning takes place in a spatially delimited region between the points that are determined by the three 3D spatial coordinates mentioned initially. Otherwise, no sufficient precision in the direction given by the normal vector would be possible; instead, this vector would have too great a parallel offset from the corrosion site outside of the stated region of the plane.

In a particularly preferred embodiment, it can be provided that the normal vector for the projection is placed in the geometrical center of gravity of the 3D spatial coordinates.

For the method according to the invention or for use with an apparatus according to the invention, it is necessary to know the 2D spatial coordinates of the measurement locations or at least one of the electrodes of the electrode array relative to a predetermined coordinate system, namely in order to be able to configure the three spatial coordinates as a whole.

In this connection, in an assumption, the coordinate system can have its origin at the location of one of the electrodes of an electrode array, where then, the coordinates of all the electrodes in the x-y plane or the plane of the concrete surface are known, i.e. as 2D coordinates, because of the fixed relative placement of the electrodes. Such a determination of the 2D coordinates can already be sufficient if the method is only supposed to be carried out at one measurement location, using the method according to the invention, in order to thus determine the direction to and distance from a corrosion site at this measurement location.

In another preferred embodiment of the method, however, it is considered advantageous if the electrode array, having at least two, preferably three electrodes fixed in place relative to one another, can be moved over the surface of a concrete to be tested, and is moved, and measurements are carried out, according to the method according to the invention, at several locations of the surface. In the case of a variant in which three electrodes fixed in place are provided, one of the electrodes can be situated at the reference location and two at the measurement locations. When the electrode array is moved, the electrode at the reference location is always moved with it, in this case.

It is considered to be preferred if the 2D coordinates of the electrodes in the x-y plane or the plane of the concrete are determined relative to an external coordinate system in which the electrode array can move freely.

For example, it can be provided, for free movement and perfect contacting of the electrodes with the concrete surface, that the electrodes are configured as wheel electrodes that accordingly have wheel-shaped or roller-shaped electrodes, with which the concrete is contacted, particularly continuously, even when the electrode array is shifted. In this connection, the electrodes can have a damp surface, independent of the type of configuration, and to create optimal contacting.

In this connection, it can be provided to determine the 2D coordinates of at least one of these electrodes of the electrode array, relative to the predetermined external coordinate system, for example by a measurement of the movement range of the electrodes by a movement sensor on this electrode, or also by a navigation system, particularly an external navigation system.

With such a navigation system, electrodes or at least one electrode, for example, can be observed by at least one camera, relative to locally fixed reference points, in order to then draw a conclusion concerning the position in the selected coordinate system from the position in the camera image.

After an origin has been defined, for example by setting the electrode array down onto the surface of a concrete to be examined, for the first time, it can also be determined, by a measurement of the movement range by a movement sensor mentioned previously, how far the electrode array was moved, starting from this origin, particularly in a specific direction.

Here, there is also the possibility of measuring not only the movement range in a specific direction, but in general, a movement range and a movement direction in any desired manner within a plane, i.e. here, for example, along the surface of a concrete to be tested, and thus in the x-y plane [sic—lower-case x], and of determining the coordinates of the electrodes from the measurements, namely specifically in that the movement ranges are determined with at least two movement sensors, for example wheel sensors, that are spaced apart, particularly provided on two electrodes. Thus, a difference in the movement range between two electrodes is obtained, for example, if the entire array was moved not in a straight line, but rather along a curve-shaped trajectory, for example.

Accordingly, the coordinate of the measurement location or of the three electrodes involved in the measurement can be determined by a data-processing system that registers the movement ranges of at least one, preferably a plurality of movement sensors, proceeding from the coordinate origin originally established at the time of a measurement, according to the method determined initially.

In this connection, determination of the coordinate of one of the electrodes is sufficient, as mentioned initially, because the other electrodes can be determined directly from this, on the basis of the fixed relative placement with regard to one another. This holds true for the determination of the movement range by a sensor, as described, and for the use of an external navigation system.

Using the method according to the invention, the possibility exists of moving the electrode array along a predetermined trajectory, over the surface of a concrete, or also of recording the trajectory during a movement of the electrode array over the surface of the concrete, and of determining the direction toward and/or the distance from a corrosion site a plurality of times, along the trajectory, continuously or at discrete intervals, for example by the direction and/or length of the mathematically projected normal vector at the location of the measurement.

Accordingly, a plurality of measurements for the direction and/or the distance mentioned initially is obtained on the surface of a concrete, or, in the preferred embodiment, for the direction and/or length of the projected normal vector, so that accordingly, information is also obtained with regard to a plurality of locations on the surface of the concrete as to the direction and how far away from the respective measurement position a potential corrosion site is located.

Preferably, it can be provided here to store the values determined in memory, together with the location coordinates, for every location of the determination of direction and/or distance or direction and/or length of the projected normal vector.

Thus, the preferred possibility results from this of generating a map representation from the stored values (direction and/or distance or length as a function of the measurement location coordinate) and displaying it, for example on a display or also as a printout, in which the length and/or direction of the projected normal vector is represented on the map-type representation as an arrow, for example, for every location of the determination of the projected normal vector.

Accordingly, a graphic representation of the concrete surface is obtained, with the respective measurement positions where accordingly, an arrow or also simply a line is represented at every measurement position, which points in a specific direction and has a specific length. The direction toward the potential corrosion site is indicated by the direction of the arrow or line, while the length, as stated initially, defines the distance to the corrosion site, in the sense that the longer the arrow or line, the closer the corrosion site is situated to the location of the measurement.

Furthermore, it can also be provided that a graphic representation of distance/length and/or direction is displayed to a user of the electrode array at the location of the determination of distance and/or direction or the length and/or the direction of a mathematically projected normal vector, particularly as an arrow representation. For this purpose, it can be provided that an apparatus for implementing the method has a display unit, for example a display that shows an arrow or a line in a specific direction and/or in a specific length.

Likewise, the possibility exists here of undertaking an actual optical projection of an arrow having a specific direction and a specific length, corresponding to the values of distance/length and direction.

BRIEF DESCRIPTION OF THE DRAWING

An embodiment of the invention is shown schematically in the following figures. Therein:

FIGS. 4A and 4B show the mathematical relationship, according to formulas, in the implementation of the method.

DETAILED DESCRIPTION OF THE INVENTION

Figure 1:
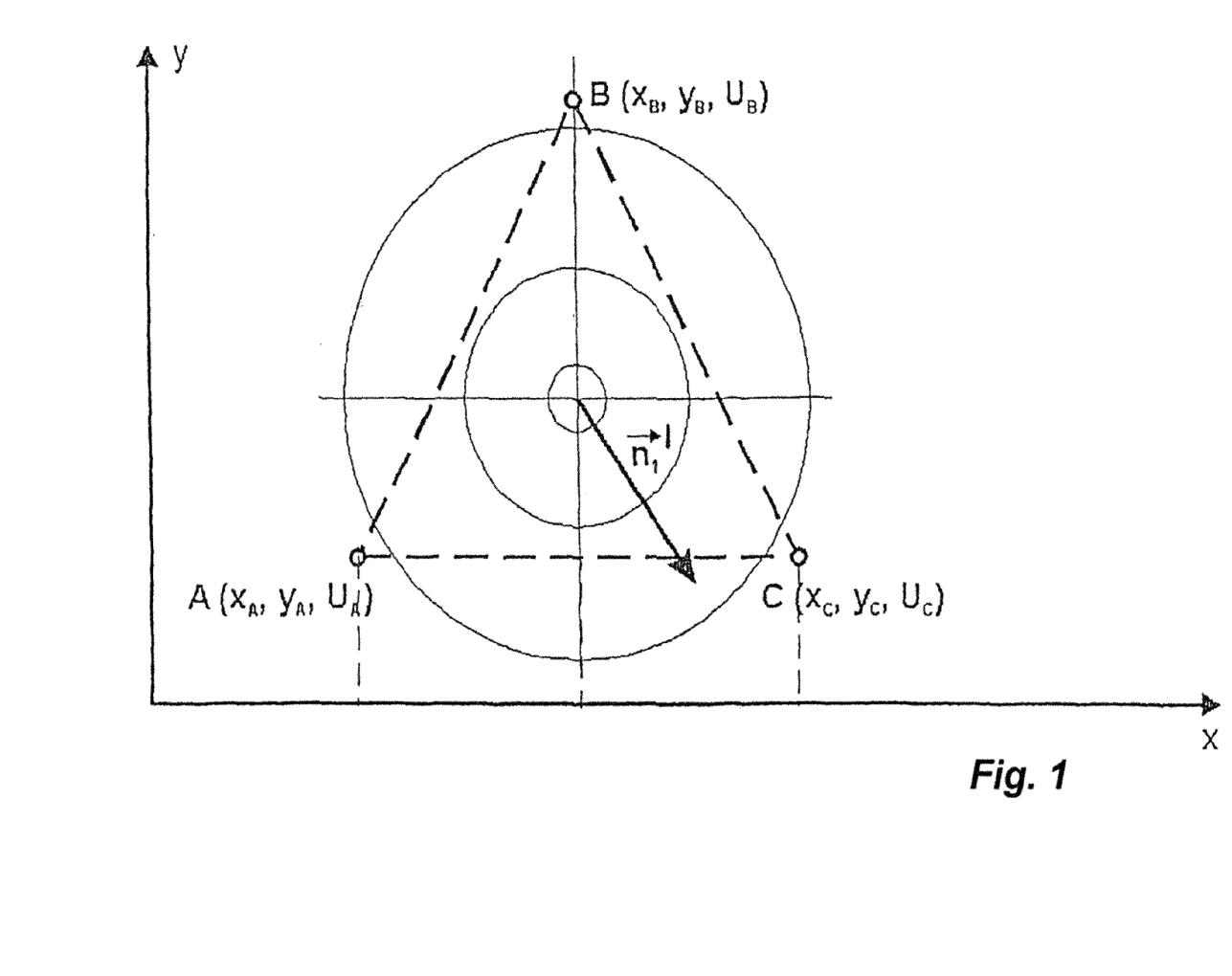
FIG. 1 shows the placement of the measurement points of electrodes A, B, and C in the x-y plane of a selected coordinate system.

FIG. 1 shows an electrode array of an apparatus for carrying out the method according to the invention, in a schematic top view. In this schematic representation, the electrode array has three electrodes A, B, and C that are laid on the surface of a body of reinforced concrete and contact it, where a reference coordinate system is selected in such a manner that the x-y plane of this coordinate system coincides with the surface of the concrete or is parallel to it.

Thus, each of the three electrodes A, B and C has 2D location coordinates in the x-y plane of the coordinate system, namely the electrode A has the coordinate (XA, YA), the electrode B has the coordinate (XB, YB), and the electrode C has the coordinate (XC, YC). In a simplified embodiment, the selected coordinate system can have its origin at the location of one of the electrodes, as was mentioned initially; likewise, it can be provided to orient the origin outside the electrode array, particularly if a plurality of measurements are supposed to be carried out using the electrode array at different positions within the coordinate system and thus on the surface of the concrete.

Here, use an electrode array has three electrodes. In this connection, this is the minimum number of required electrodes; accordingly, it can also be provided to use electrode arrays having more than three electrodes. For such arrays, the statements made here apply analogously. In this connection, it is essential that all the electrodes of the electrode array have a fixed relative distance from one another, and that one of the electrodes of the electrode array is situated at the reference location or defines it, so that the potential at the other electrodes of the electrode array is measured relative to the electrode at the reference location.

As an example, let it be assumed here that the electrode A forms an electrode at the reference location, and accordingly, the potentials at the locations of the electrodes B and C are measured relative to the potential at the electrode A. Fundamentally, however, it is unimportant which of the three electrodes that are present is situated at the reference location. Here, the electrodes are provided in such a manner that their contact points on the concrete form a triangle.

For implementation of the method, it can therefore be assumed that the potential at the location of the electrode A is stable, so that the relative measurement at the location of the other electrodes of the electrodes B and C is possible. In place of an electrode array having three locally fixed electrodes, according to FIG. 1, the method can also be carried out using one electrode and at least two potential measurements with this one electrode relative to a reference potential, or with other electrode configurations. The essential thing is that potential values are obtained for at least three locations.

The measurements of the potentials UB at the location of the electrode B and UC at the location of the electrode C, measured against the electrode at the location A, can now be used further, in order to form spatial coordinates of each of the electrodes A, B, and C, together with the location coordinates in the x-y plane, namely the spatial coordinates for a point A having the position (XA, YA, UA=zero), a point B having the position (XB, YB, UB), and a point C having the position (CX, YC, UC) in the selected coordinate system.

In a coordinate system in which the measured potential is plotted perpendicular to the selected x-y plane, in other words, for example, in the z direction, the points A, B, and C established in this manner form a spatial arrangement relative to one another that defines a mathematical plane E, i.e. these three points or, in the case of a plurality of electrodes, also a plurality of points, lie within this plane E.

Figure 2:
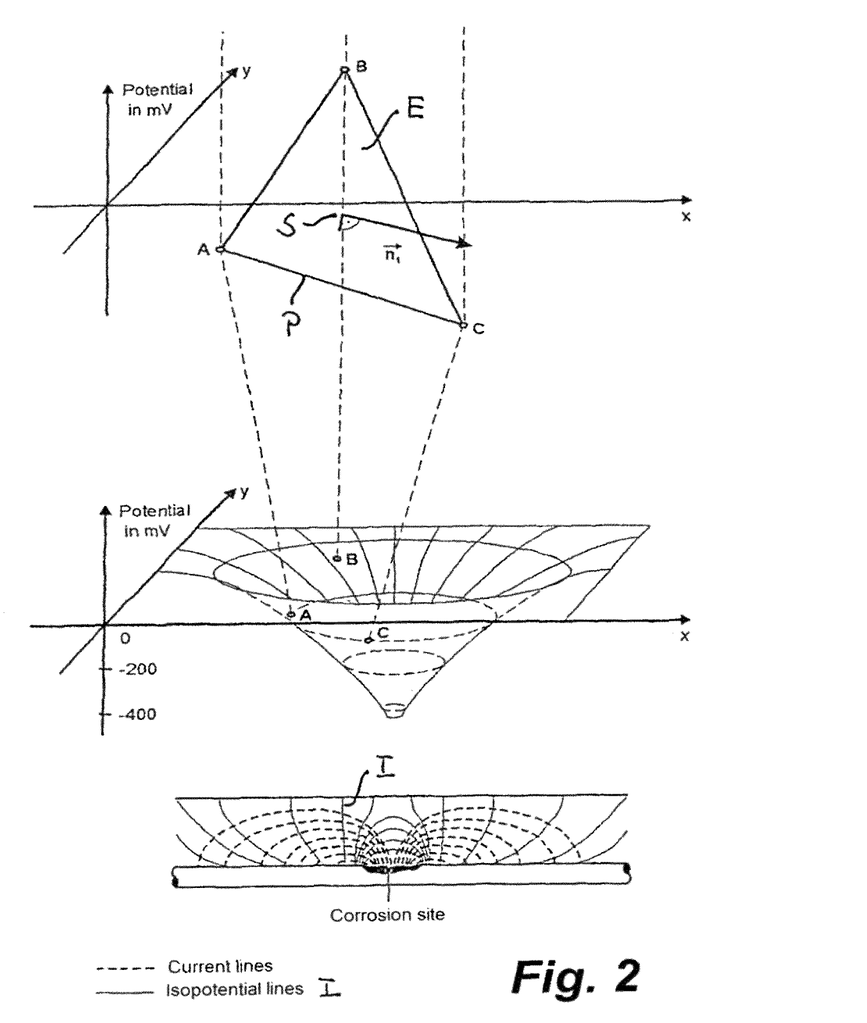
FIG. 2 is an idealized view of the potential progression at a corrosion site of a reinforcement rod and a representation of the potential measurements.

In FIG. 2, in the upper figure, the placement of the points A, B, and C in the selected coordinate system is shown, where it is made clear, by making reference to the lower figure, that the points A, B, and C represent the values of the potential at the location of the x-y coordinate, with regard to their z coordinate. Here, in the schematic representation, an ideal funnel-shaped potential is schematically shown at a corrosion site K.

Using the method according to the invention, the length and/or the direction can now be determined from the mathematical projection of the standardized normal vector $n_1$ on this mathematical plane, determined in this manner, where the projection takes place mathematically in the x-y plane of the selected coordinate system or a plane parallel to it. In FIG. 2, top, a normal vector $n_1$ is represented symbolically, with reference to the triangular enclosed area ABC, which vector stands on the plane E that has been formed and has its origin in the geometric center of gravity between the points A, B, and C in space, in the representation selected here, i.e. in the geometric center of gravity S of the polygon P that encloses the points A, B, and C and is accordingly triangular, in the present case.

FIG. 1 shows the projection of the normal vector, because it represents a top view of the x-y plane. In this connection, as explained initially, the direction of the normal vector, i.e. the angle relative to the axis of the coordinate system, here of the y axis or also of the x axis of the coordinate system, provides information concerning where the corrosion site is localized, relative to the measurement location.

Here, once again, the geometric center of gravity in the x-y plane, between the points A, B, and C, for example, can be viewed as the measurement location. In this connection, the length of the projected normal vector is a measure for the distance. The longer the normal vector, the less the distance from the corrosion site, because the normal vector inclines more and more into the x-y plane with reference to the potential progression in the center diagram of FIG. 2, and thus the projection of the standardized normal vector precisely determines the location of the corrosion site.

Figure 3:
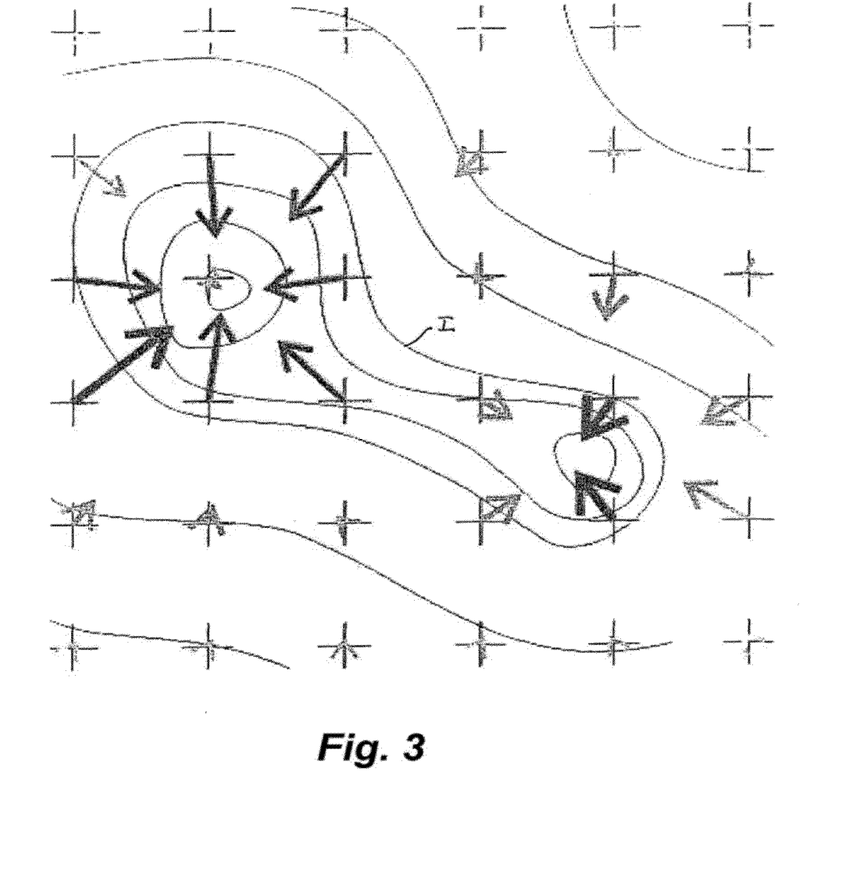
FIG. 3 is a graphic representation of the values of direction and length of the projection of the normal vector for a plurality of measurement positions.

FIG. 3, in a clear figure, shows the representation in the form of a map, in which the length and the direction of the projected vectors are drawn in for different measurement points, each of which is symbolized by a cross. Each cross represents a measurement point in the x-y plane of the selected coordinate system and thus in the surface of the concrete.

Here, the measurement point can be given by the center of gravity between the electrodes A, B, and C, or also by the location of one of the electrodes, for example the electrode at the reference location. In total, the measurement point can be any point within the area of the polygon that spans the locations of the electrodes A, B, and C in the x-y plane, as shown in FIG. 1 by the triangular area shown with a broken line.

Accordingly, in FIG. 3 a map view is shown that has a plurality of arrows here, where it is evident that a plurality of arrows point in the direction of a corrosion site with their points. In this connection, it can be provided to also represent isopotential lines I in the map representation, particularly lines that can be derived from the measurements of the potentials.

Figure 4B:
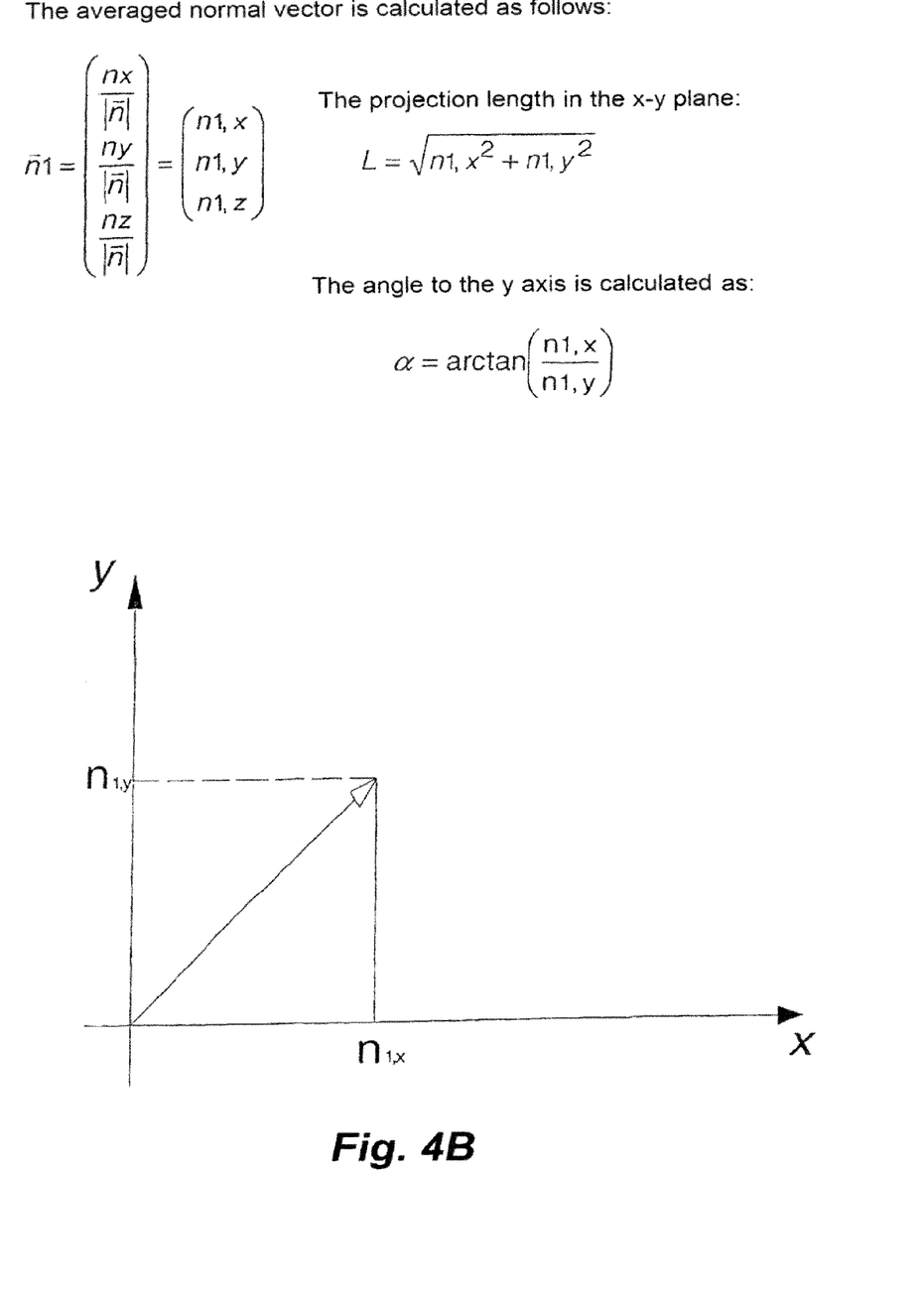

FIGS. 4A and 4B illustrate a possible example of the mathematical method of procedure in the implementation of the method according to the invention, using an apparatus according to the invention. It can be seen here that a mathematical plane can be described using the spatial coordinates XA, YA, UA, as well as XB, YB, UB, and XC, YC, UC that are formed from the 2D coordinates of the electrodes A, B, C as well as the respective potentials there for example in the point direction form.

The further calculations show the determination of the normal vector in its components NX, NY, and NZ by changing the representation of the plane in the point direction form and assuming that the component of the normal vector is set NY=1, in order to solve the equation system. In this way, the standardized normal vector can be determined, and with it, the projection length in the x-y direction, and, as an example, the angle alpha relative to the y axis of the selected coordinate system in the x-y plane.

Thus, the length and the direction of the normal vector are obtained, where the values obtained can be used not only for the map representation described above, but also in an individual case, at every measurement location, in order to undertake an actual graphic representation of the measurements, for example by a display unit or an actual optical projection of an arrow or a line having the specific length and the specific direction, i.e. at an angle to a selected axis of the coordinate system.

Accordingly, concrete surfaces can be tested in a simple manner using the invention, and preferably, corrosion sites of the reinforcement, in the depths of the concrete, can be graphically displayed.

The invention claimed is:

1. A method of determining the location of a corrosion site in a body of reinforced concrete, the method comprising the steps of:
    engaging three spaced electrodes with respective measurement points on a surface of the concrete body, the measurement points defining an X-Y measurement plane and lying at respective X and Y coordinates on the X-Y measurement plane;
    measuring with the electrodes on the surface at each of the measurement points respective actual-value voltages;
    using a data processing system to calculate for each of the measurement points a Z coordinate spaced perpendicularly from the X-Y measurement plane by a distance proportional to the respective measured voltage;
    defining a planar polygon having three corners each with the X, Y coordinates of a respective one of the measurement points and spaced from the respective measurement points by the respective Z coordinate, whereby the planar polygon is tipped relative to the measurement plane when all the measured voltages are not identical; and
    projecting from the planar polygon perpendicularly onto the measurement plane a normalized vector and establishing as a direction from the measurement points to the corrosion site an extension of the normalized vector parallel to the measurement plane.

2. The method according to claim 1, further comprising the step of:
    starting the normalized vector from a geometric gravity of the points.

3. The method according to claim 1, further comprising the step of:
    determining a 2D coordinate of at least one of the measurement locations relative to the predetermined coordinate system by a navigation system by means of which a location in the coordinate system of an electrode used for potential measurement is determined.

4. The method according to claim 1, further comprising the step of:
    performing the potential measurement at two of the measurement locations with a single electrode relative to an electrode at the third location serving as a reference location.

5. The method according to claim 4, wherein the potential measurement is undertaken by an electrode array having two electrodes fixed in position relative to one another at the respective measurement locations, the electrode at the reference location also being fixed in place relative to the electrodes at the measurement locations, at least the electrodes at the measurement locations being contacted with the surface of a reinforced concrete body to be tested.

6. The method according to claim 5, further comprising the steps of:
    moving the electrode array over the surface of the concrete body to be tested by wheel electrodes,
    determining a 2D coordinate of at least one of the electrodes of the electrode array relative to the predetermined coordinate system by measuring a movement range of the electrode by a movement sensor on this electrode.

7. The method according to claim 6, further comprising the step of:
    determining a movement range and movement direction of at least one electrode by measuring movement ranges of at least two movement sensors that are spaced apart and that are provided on respective electrodes.

8. The method according to claim 5, further comprising the step of:
    moving the electrode array over the surface of the concrete body along a predetermined trajectory, or
    recording a trajectory during movement of the electrode array over the surface of the concrete body, and
    determining the direction or distance to a corrosion site a plurality of times along the trajectory.

9. The method according to claim 1, further comprising the steps, for each measurement location, of:
    determining direction or distance, and
    storing this direction or this distance in memory together with the respective X, Y coordinates.

10. The method according to claim 9, further comprising the step of:
    generating a map representation from a stored values,
    displaying a map representation on a display or a printout, and
    representing the direction or the distance on the map for every location of the determination of direction or distance.

11. The method according to claim 5, further comprising the step of:
    displaying a graphic representation of distance or direction to a user of the electrode array at the location of the determination of direction or distance to a corrosion site as an arrow.

12. The method according to claim 11, wherein the arrow is displayed on a display unit or by actual projection of the arrow on the surface of the concrete.

* * * * *